United States Patent [19]

Ikuta et al.

[11] Patent Number: 4,833,160

[45] Date of Patent: May 23, 1989

[54] 3-(3,5-DI-TERT-BUTYL-4-HYDROXY BENZYLIDENE)-2-PYRROLIDONE AND N-SUBSTITUTED DERIVATIVES THEREOF

[75] Inventors: Hironori Ikuta; Youji Yamagishi; Kozo Akasaka; Isao Yamatsu; Seiichi Kobayashi; Hiroshi Shirota; Kouichi Katayama, all of Ibaraki, Japan

[73] Assignee: Eisai Co., Ltd., Tokyo, Japan

[21] Appl. No.: 856,068

[22] Filed: Apr. 23, 1986

[30] Foreign Application Priority Data

May 9, 1985 [JP] Japan .................................. 60-96799

[51] Int. Cl.$^4$ .................. A61K 31/40; C07D 207/276; C07D 207/27
[52] U.S. Cl. .................................. 514/424; 514/425; 548/542; 548/543
[58] Field of Search .............. 548/551, 550, 542, 543; 514/424, 425

[56] References Cited

U.S. PATENT DOCUMENTS 4,581,364 4/1986 Weber et al. ....................... 548/551

FOREIGN PATENT DOCUMENTS 0001601 5/1979 European Pat. Off. ............ 514/424
0104864 8/1981 Japan ................................. 514/424
1012660 1/1986 Japan ................................. 548/493

Primary Examiner—David B. Springer
Attorney, Agent, or Firm—Flynn, Thiel, Boutell & Tanis

[57] ABSTRACT 3-(3,5-di-tert-butyl-4-hydroxy-benzylidene)-2-pyrrolidone and N-substituted derivatives thereof are described. The substituent includes alkyl, alkoxy, alkynyl phenyl-alkylene, hydroxy-alkylene and amino-alkylene. They are effective as an anti-inflammatory, analgesic and antithermic agent, and they have a low toxicity.

20 Claims, No Drawings

3-(3,5-DI-TERT-BUTYL-4-HYDROXY BENZYLIDENE)-2-PYRROLIDONE AND SUBSTITUTED DERIVATIVES THEREOF

The invention relates to 2-pyrrolidone derivatives, including 3-(3,5-di-tert-butyl-4-hydroxybenzylidene)-2-pyrrolidone and N-substituted derivatives thereof. The substituent includes alkyl, alkoxy, alkynyl, phenyl-alkylene, hydroxy-alkylene and amino-alkylene. They are effective especially as an anti-inflammatory, analgesic and antithermic agent, and they have a low toxicity. The invention further relates to processes for preparation of the same and a pharmaceutical composition which comprises the same and a pharmaceutically acceptable carrier. The 2-pyrrolidone derivatives exert excellent pharmaceutical effects. In the composition, an invention compound is used in a therapeutically effective amount. The invention compounds are defined by the formula (I):

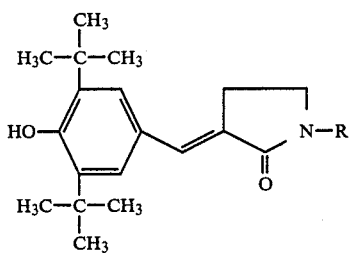
(I)

wherein R represents a hydrogen atom, a lower alkyl, a lower alkoxy or a lower alkynyl group or a group of the formula:

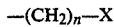
—(CH$_2$)$_n$—X wherein X represents a phenyl or a hydroxyl group or a group of the formula:

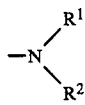

wherein R$^1$ and R$^2$ may be the same or different from each other and each represents a hydrogen atom or a lower alkyl group; and
n represents an integer of 1 or 2;
a pharmaceutically acceptable salt thereof; a process for the preparation of the same; and a pharmaceutical comprising the same as an active ingredient.

The term "lower alkyl group" as used above in defining R, R$^1$ and R$^2$ includes straight-chain or branched alkyl groups having one to six carbon atoms, such as methyl, ethyl, n-propyl, isopropyl, n-butyl, isobutyl, 1-methylpropyl, tert-butyl, n-pentyl, 1-ethylpropyl, isoamyl and n-hexyl groups.

The lower alkoxy and lower alkynyl groups as described above include those derived from the above-mentioned lower alkyl groups.

The compounds (I) of the present invention may be converted into the corresponding sodium or potassium salt if required. When R is a group of the formula

it ma be further converted into a pharmaceutically acceptable salt thereof with an inorganic acid such as hydrochloric, hydrobromic or hydroiodic acid or an organic acid such as maleic, fumaric, succinic, malonic, acetic, citric or methanesulfonic acid.

The compounds (I) of the present invention may be prepared by various processes. Some typical examples thereof are as follows.

Preparation process 1:

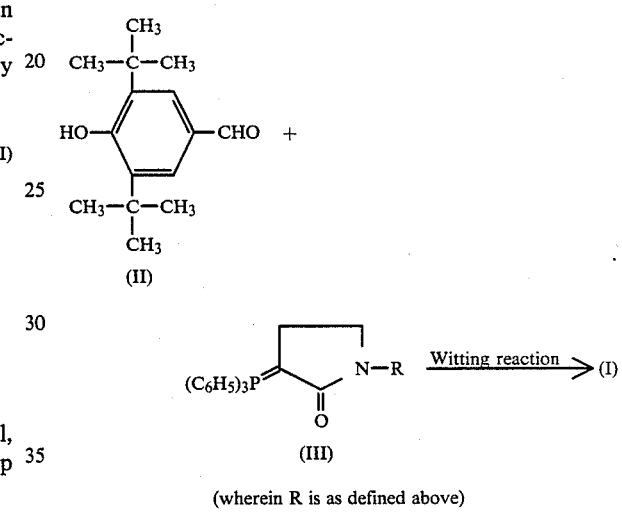

(wherein R is as defined above)

That is, 3,5-di-tert-butyl-4-hydroxybenzaldehyde (II) is reacted with a Wittig reagent (III) in a conventional manner to give the desired compounds (I). Any solvent which does not participate in the reaction may be employed. Examples of a preferred solvent are dimethylformamide (DMF), dimethyl sulfoxide (DMSO), ethanol, ethyl acetate and benzene. The reaction may be carried out at approximately 0° to 150° C., preferably 30° to 100° C.

Preparation process 2:

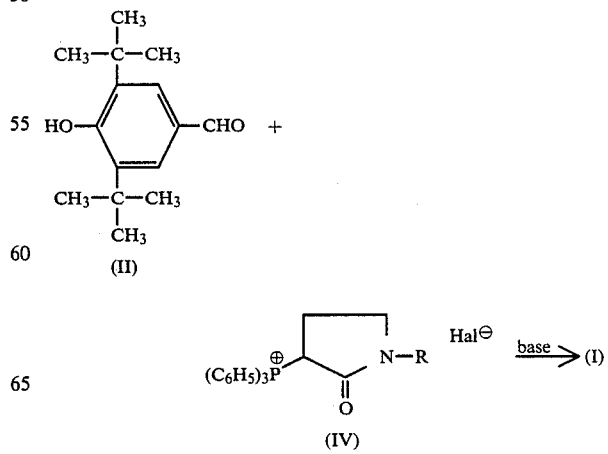

(wherein R is as defined above and Hal represents a halogen atom).

That is, 3,5-di-tert-butyl-4-hydroxybenzaldehyde (III) is reacted with a Wittig salt (IV) in the presence of a base to thereby perform the Wittig reaction, thus giving the desired compound (I). Examples of the base are organic bases such as triethylamine and pyridine and inorganic bases such as sodium carbonate and potassium carbonate. Any solvent which does not participate in the reaction may be employed. Examples of a preferred solvent are dimethylformamide (DMF), dimethyl sulfoxide (DMSO), ethanol, ethyl acetate and benzene. The reaction may be carried out at approximately 0° to 150° C., preferably 30° to 100° C.

The above shown compound (IV) is derived from a novel intermediate compound having the formula (VII):

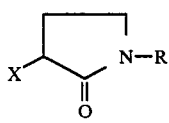

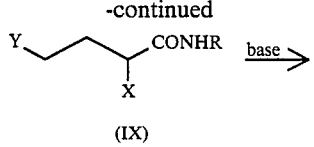

(IX)

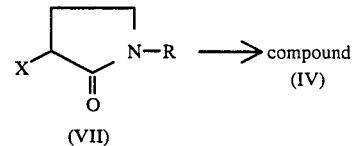

(VII)

Y is a halogen or an organic sulfonyloxy group, X is a halogen and R is a lower alkoxy group.

In the process as shown above, the compound (VII) is obtained by the ring formation reaction with a base such as NaH, $K_2CO_3$ and sodium alkoxide in a solvent such as ethanol and benzene at a temperature of minus 50° to plus 100° C. The compound (IV) is obtained by a reaction with triphenyl phosphine. In this step, triethyl phosphite may be alternatively used to obtain a Wittig reagent.

An embodiment in which R is methoxy and X and Y is each bromine is below shown.

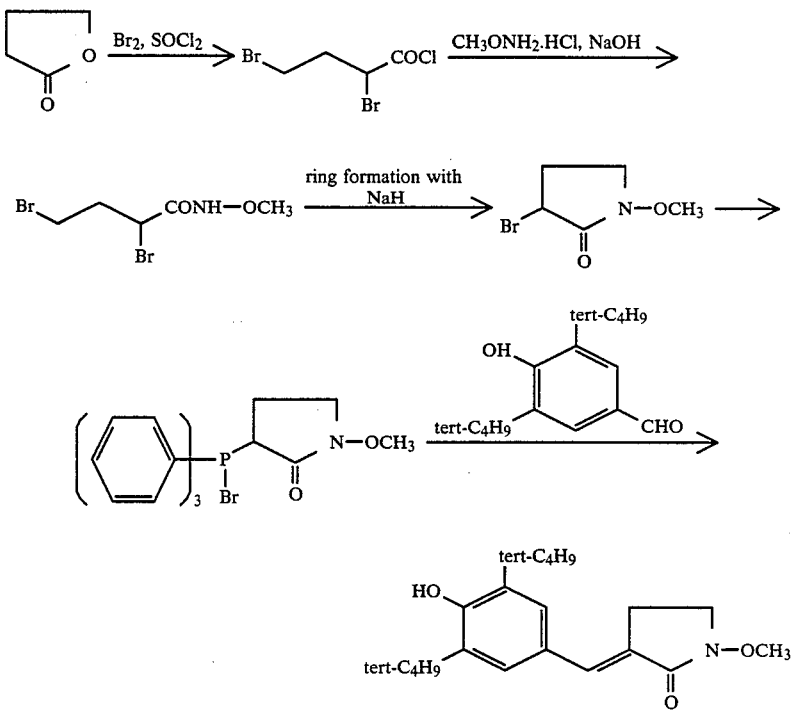

in which R is defined as above and X is a halogen. It is preferable that R is methoxy and X is bromine.

A process for preparing the intermediate compound (VII) is illustrated below.

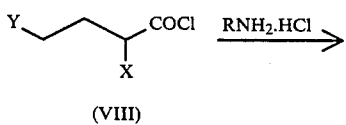

(VIII)

Preparation process 3:

The desired compounds (I), wherein R is a lower alkyl or a lower alkynyl group or a group of the formula, $-(CH_2)_n-X$, wherein X is as defined above, may be prepared in the following manner.

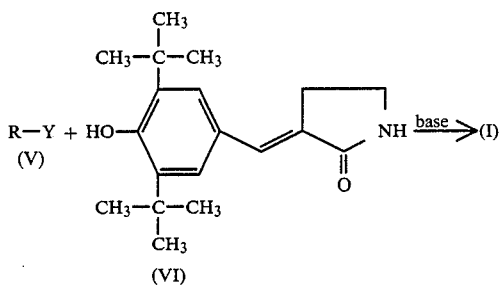

(wherein R is as defined above; and

Y represents a halogen atom or an organic sulfonyloxy group such as a mesyloxy or a tosyloxy group)

That is, the compound (V), which serves as an alkylating agent, is reacted with the compound (VI) of the present invention in the presence of a base such as sodium hydride, sodium amide or potassium tert-butoxide to give the desired compound (I). Any solvent which does not participate in the reaction may be employed. Examples of a preferred solvent are dimethylformamide (DMF), dimethyl sulfoxide (DMSO), benzene, tetrahydrofuran (THF) and tert-butanol. The reaction may be carried out at approximately −20° to 100° C., preferably 0° to 30° C.

To further illustrate the present invention, and not by way of limitation, typical examples of the compounds of the invention will be given.

N-methyl-3-(3,5-di-tert-butyl-4-hydroxybenzylidene)-2-pyrrolidone,
N-ethyl-3-(3,5-di-tert-butyl-4-hydroxybenzylidene)-2-pyrrolidone,
3-(3,5-di-tert-butyl-4-hydroxybenzylidene)-2-pyrrolidone,
N-methoxy-3-(3,5-di-tert-butyl-4-hydroxybenzylidene)-2-pyrrolidone,
N-(2-dimethylaminoethyl)-3-(3,5-di-tert-butyl-4-hydroxybenzylidene)-2-pyrrolidone,
N-benzyl-3-(3,5-di-tert-butyl-4-hydroxybenzylidene)-2-pyrrolidone,
N-propargyl-3-(3,5-di-tert-butyl-4-hydroxybenzylidene)-2-pyrrolidone,
N-(2-hydroxyethyl)-3-(3,5-di-tert-butyl-4-hydroxybenzylidene)-2-pyrrolidone,
N-n-butyl-3-(3,5-di-tert-butyl-4-hydroxybenzylidene)-2-pyrrolidone,
N-(2-diethylaminoethyl)-3-(3,5-di-tert-butyl-4-hydroxybenzylidene)-2-pyrrolidone,
N-ethoxy-3-(3,5-di-tert-butyl-4-hydroxybenzylidene)-2-pyrrolidone,
N-hexyl-3-(3,5-di-tert-butyl-4-hydroxybenzylidene)-2-pyrrolidone and
N-n-butoxy-3-(3,5-di-tert-butyl-4-hydroxybenzylidene)-2-pyrrolidone.

Each of the 2-pyrrolidone derivatives provided by the present invention is a novel compound which has never been reported in any literature and exhibits a low toxicity and a remarkable anti-inflammatory effect.

Anti-inflammatory agents may be roughly classified into the following four groups, i.e. steroidal hormones, nonsteroidal agents, antiphlogistic enzymes and immunosuppressive agents. Among these four groups, nonsteroidal agents are the most important, which causes recent lively attempts to develop nonsteroidal anti-inflammatory agents all over the world.

Nonsteroidal agents which are frequently used at present include indoleacetic acid derivatives such as indomethacin; phenylacetic acid derivatives such as ibufenac and ibuprofen; salicylic acid derivatives such as aspirin, salicylic acid and salicylosalicylic acid; anthranilic acid derivatives such as mefenamic acid and flufenamic acid; pyrazolidinedione derivatives such as phenylbutazone, oxyphenylbutazone and ketophenylbutazone; and basic drugs such as benzydamine, mepirizol and tinoridine.

However these nonsteroidal agents have a serious disadvantage from a clinical viewpoint. That is, they exhibit a side effect of inducing gastric and renal disorders. Thus there has been still attempted to develop better nonsteroidal anti-inflammatory agents all over the world.

Under these circumstances, we have studied to develop novel anti-inflammatory agents for a long time and consequently found that 2-pyrrolidone derivatives of the general formula (I), which have a chemical structure different from those of conventional nonsteroidal anti-inflammatory agents, exert an excellent anti-inflammatory effect.

Accordingly the compounds of the present invention are 2-pyrrolidone derivatives of the general formula (I):

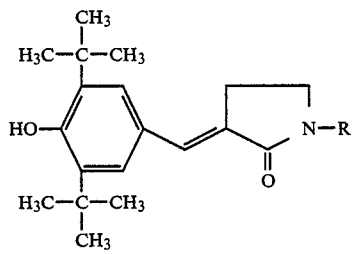

wherein R represents a hydrogen atom, a lower alkyl, a lower alkoxy or a lower alkynyl group or a group of the formula:

—(CH$_2$)$_n$—X wherein X represents a phenyl group or a hydroxyl group or a group of the formula:

wherein R$^1$ and R$^2$ may be the same or different from each other and each represents a hydrogen atom or a lower alkyl group; and n represents an integer of 1 or 2:

and a pharmaceutically acceptable salt thereof.

Each compound of the present invention is valuable as an anti-inflammatory, analgesic and antithermic agent of low toxicity. Further it is pharmaceutically characterized by the following facts.

1. It has a wider safe range than conventional anti-inflammatory agents such as indomethacin, ibuprofen and piroxicam.

2. It further exerts lipoxygenase inhibition and antioxidant effects which are never observed in conventional nonsteroidal anti-inflammatory agents.

The compound of the present invention may be applied to treatment of conditions to which conventional anti-inflammatory agents are applied. Examples of these conditions are arthritis, rheumatism, neuritis, arthalgia, neuralgia, cold syndrome, acute and chronic bronchitis, traumatic and postoperative inflammation, pyrexia and ache including dentalgia and headache.

To illustrate the usefulness of the compounds of the present invention in detail, the following pharmacological examples will be given.

Pharmacological Example 1

Effect of lowering local surface temperature at inflammation (1) Experimental Method 0.05 ml of a suspension of butter bacillus in liquid paraffin (10 mg/ml) was injected into the sole of the right hind foot of a male Fisher rat aged six weeks to thereby induce adjuvant inflammation. After three to five days, the surface temperature of the inflammatory foot was constantly higher by 8° to 10° C. than that of a normal foot. The test compounds as described hereinbelow and control compounds (i.e. indomethacin and pyroxycam) were each suspended in a 5% aqueous solution of gum arabic and orally administered to the rat in a dose of 5 ml/kg body weight. The local surface temperature of the inflammatory site was determined after two, four and six hours according to the method of H. Shirota et al. (cf. J. Pharmacol. Methods, 12, 35–43 (1984)). The dose required for lowering the surface temperature by at least 2° C. below that prior to the administration was calculated by averaging data of two animals, thus determining the anti-inflammatory titer of each test compound.

(2) Test compound

Compound A: N-methyl-3-(3,5-di-tert-butyl-4-hydroxybenzylidene)-2-pyrrolidone,

Compound B: N-methoxy-3-(3,5-di-tert-butyl-4-hydroxybenzylidene)-2-pyrrolidone and Compound C: 3-(3,5-di-tert-butyl-4-hydroxybenzylidene)-2-pyrrolidone.

(3) Result

Table 1 shows the result.

TABLE 1

| Compound | Dose (mg/kg) required for lowering local temperature at inflammatory site by at least 2° C. |
|---|---|
| Compound A | 1 |
| Compound B | 0.3 |
| Compound C | 0.3 |
| Indomethacin | 0.3 |
| Piroxicam | 0.3 |

Pharmacological Example 2

Effect of suppressing carrageenan edema at foot-sole (1) Experimental Method

Male Fisher rats aged five weeks were classified into groups each having five animals. Each test compound was suspended in a 5% aqueous solution of gum arabic and administered to each rat in a dose of 0.5 m/100 g body weight. After one hour, a 1% carrageenan solution was injected into the sole of the right hind foot of the animal to thereby induce inflammation. Three hours after the carrageenan injection, the volume of the sole of each hind foot of the animal was measured to calculate the volume-gain of the foot-sole to which carrageenan was injected. The obtained data was compared with those of the control groups, thus determining the suppression ratio of the test compound. The same test compounds as used in Pharmacological Example 1 were used.

(2) Result

Table 2 shows the result.

TABLE 2

| Compound | Dose (mg/kg) | Suppression ratio |
|---|---|---|
| Compound A | 10 | 36.1 |
| Compound B | 10 | 36.4 |
| Compound C | 10 | 38.5 |
| Indomethacin | 10 | 37.7 |

Pharmacological Example 3

Effect of inducing gastric ulcer (1) Experimental Method

A male Fisher rat aged seven weeks was kept fasting for 24 hours and then each test compound suspended in a 5% aqueous solution of gum arabic was orally administered thereto. After six hours, the 50% ulcer dose of the test compound was determined from hemorrhagic maculas observed in the tunica mucosa ventriculi.

(2) Result

Table 3 shows the result, wherein each $UD_{50}$ represents a 50% ulcer inducing dose (mg/kg).

TABLE 3

| Compound | $UD_{50}$ (mg/kg) |
|---|---|
| Compound B | 473.0 |
| Compound C | 75.8 |
| Indomethacin | 7.8 |
| Piroxicam | 23.1 |

The results of these Pharmacological Examples clearly indicate that each compound of the present invention exhibits an intense anti-inflammatory effect hardly accompanied by a side effect of inducing gastric disorder which is frequently observed in the case of conventional anti-inflammatory agents. Therefore the compounds of the present invention are significantly excellent as an anti-inflammatory agent which should be continuously taken for a prolonged period of time.

Acute Toxicity Test

LD 50 of the compound B, falling within the scope of the invention, was investigated in respect to acute toxicity, using rats and mice. Results are shown in Table 4.

TABLE 4

| administration method | $LD_{50}$ and Confidential Range | | | |
|---|---|---|---|---|
| | rats | | mice | |
| | male | female | male | female |
| oral | 354.2 | 161.2* | 4000~2000 | 6873 |
| abdominal | 96.7* | 46.9* | 1069 | 805.4 |
| | | | 523~2270 | 443.9~1549.3 |
| hypodermic | 806.4* | 291 | >4000 | >4000 |
| | | 124~476 | | |

Note
*Values were calculated according to Behrens-Karber method. The oral administration was conducted after a fasting treatment for 17 to 24 hours.

Thus the present invention is highly valuable.

In using the compounds of the present invention as anti-inflammatory drugs, they are administered perorally or non-perorally (i.e. intramuscular, subcutaneous or intravenous administration or by suppository).

The dose varies depending on the symptoms, age and individual differences of patients and is generally about 1–500 mg/day, preferably 5–300 mg/day, more preferably 10–100 mg/day, for adult human beings.

The compound of the invention can be used in the form of tablets, granules, powder, capsules, an injection liquid, suppository, a pharmaceutical formulation for external use, such as an ointment, according to a conventional practice.

In the preparation of a peroral solid product, an excipient and, if necessary, a binder, disintegrator, lubricant, coloring agent and corrigent (flavoring agent) are added to the active ingredient and the mixture is then shaped into tablets, coated tablets, granules, powder or capsules.

As the excipients, there can be used, for example, lactose, corn starch, white sugar, glucose, sorbitol, crystalline cellulose and silicon dioxide. As the binders, there can be used, for example, polyvinyl alcohol, polyvinyl ether, ethylcellulose, methylcellulose, acacia, tragacanth, gelatin, shellac, hydroxypropylcellulose, hydroxymethylpropylcellulose, hydroxypropylstarch, polyvinylpyrrolidone, white sugar and sorbitol. As the disintegrators, there can be used, for example, starch, agar, gelatin powder, crystalline cellulose, calcium carbonate, sodium hydrogencarbonate, calcium citrate, dextrin and pectin. As the lubricants, there can be used, for example, magnesium stearate, talc, polyethylene glycol, silica and hardened vegetable oils. As the colorants, there can be used those allowed as additives to medicines. As the corrigents, there can be used cocoa powder, menthol, aromatic powder, peppermint oil, borneol and cinnamon powder. Those tablets and granules can be coated suitably with sugar, gelatin, etc.

In the preparation of a liquid medicine for peroral administration, a corrigent, buffer, stabilizer, etc. are added, if necessary, to the active ingredient and the mixture is treated to form, for example, a syrup.

In the preparation of an injectable solution, a pH regulator, buffer, suspending agent, solubilizer, stabilizer, isotonizer and preservative are added, if necessary, to the active ingredient and the mixture is treated to form a subcutaneous, intramuscular or intravenous injectable solution.

As the suspending agents, there can be used, for example, methylcellulose, Polysorbate 80, hydroxyethylcellulose, acacia, tragacanth powder, sodium carboxymethylcellulose and polyoxyethylenesorbitan monolaurate. As the solubilizers, there can be used polyoxyethylene-hardened castor oil, Polysorbate 80, nicotinic acid amide, polyoxysorbitan monolaurate, Macrogol, castor oil and fatty acid ethyl esters. As the stabilizers, there can be used, for example, sodium sulfite, sodium metasulfite and ether. As the preservatives, there can be used methyl p-hydroxybenzoate, ethyl p-hydroxybenzoate, sorbic acid, phenol, cresol and chlorocresol.

To further illustrate the present invention, and not by way of limitation, the following examples will be given.

EXAMPLE 1

N-methyl-3-(3,5-di-tert-butyl-4-hydroxybenzylidene)-2-pyrrolidone 1.2 g of 3,5-di-tert-butyl-4-hydroxybenzaldehyde, 2.5 g of (N-methyl-2-pyrrolidone-3-yl)triphenylphosphonium bromide and 1.0 ml of triethylamine were heated under reflux in ethanol for two hours. After distilling the ethanol off, the residue was dissolved in chloroform, washed with water followed by a saturated saline solution and dried over anhydrous magnesium sulfate. After distilling the chloroform off, the residue was subjected to column chromatography with the use of silica gel and benzene/acetone and recrystallized from a mixture of ethyl acetate and hexane to give 1.0 g of the title compound.

m.p.: 185° C.

NMR ($\delta$, CDCl$_3$): 1.47 (18H, s), 3.50 (2H, t, J=6 Hz), 3.01 (3H, s), 5.43 (1H, s), 7.30 (1H, t, J=3 Hz) and 7.36 (2H, s).

EXAMPLES 2 TO 4

The following compounds were prepared according to the procedure of Example 1.

EXAMPLE 2

N-ethyl-3-(3,5-di-tert-butyl-4-hydroxybenzylidene)-2-pyrrolidone m.p.: 186.5° C.

NMR ($\delta$, CDCl$_3$): 1.45 (18H, s), 2.9–3.1 (2H, m), 3.3–3.6 (4H, m), 5.40 (1H, s), 7.26 (1H, t, J=3 Hz) and 7.32 (2H, s).

EXAMPLE 3

N-methoxy-3-(3,5-di-tert-butyl-4-hydroxybenzylidene)-2-pyrrolidone 27.6 g of 3,5-di-tert-butyl-4-hydroxybenzaldehyde, 54.0 g of (N-methoxy-2-pyrrolidone-3-yl)triphenylphosphonium bromide and 33.0 ml of triethylamine were heated at 50° C. in ethanol for four hours. After distilling the ethanol off, the residue was dissolved in chloroform, washed with water and then a saturated saline solution and dried over anhydrous magnesium sulfate. After distilling the chloroform off, the residue was treated with the column chromatography, using silica gel and a carrier liquid of benzene and acetone and recrystallized with a mixture of ethyl acetate and hexane to give 26.5 g of the title compound.

m.p.: 169° C.

NMR ($\delta$, CDCl$_3$): 1.46 (18H, s), 3.05 (2H, dt, J=3 Hz, 7 Hz), 3.66 (2H, t, J=7 Hz), 3.88 (3H, s), 5.44 (1H, s), 7.30 (2H, s) and 7.35 (1H, t, J=3 Hz).

EXAMPLE 4

3-(3,5-di-tert-butyl-4-hydroxybenzylidene)-2-pyrrolidone m.p.: 210° C. (dcomp.)

NMR ($\delta$, CDCl$_3$): 1.46 (18H, s), 3.13 (2H, broad, dt, J=3 Hz, 6 Hz), 3.52 (2H, t, J=6 Hz), 5.45 (1H, s), 6.98 (1H, broads), 7.32 (1H, t, J=2 Hz) and 7.37 (2H, s).

EXAMPLE 5

N-(2-dimethylaminoethyl)-3-(3,5-di-tert-butyl-4-hydroxybenzylidene)-2-pyrrolidone 500 mg of 3-(3,5-di-tert-butyl-4-hydroxybenzylidene)-2-pyrrolidone was dissolved in 5 ml of dimethylformamide and 0.2 g of sodium hydride and 0.2 g of 2-dimethylaminoethyl chloride were successively added thereto under ice-cooling. Then the obtained mixture was allowed to react for one hour at room temperature. The reaction mixture was extracted with ethyl acetate, washed with water followed by a saturated saline solution and dried over anhydrous magnesium sulfate. After distilling the ethyl acetate off, the residue was purified by column chromatography with the use of silica gel and benzene/acetone and recrystallized from ethyl acetate/hexane to give 300 mg of the title compound.

m.p.: 150° C.

NMR (δ, CDCl₃): 1.46 (18H, s), 2.26 (6H, s), 2.50 (2H, t, J=7 Hz), 2.9-3.1 (2H, m), 3.54 (4H, t, J=7 Hz), 5.37 (1H, s), 7.26 (1H, t, J=3 Hz) and 7.31 (2H, s).

EXAMPLES 6 TO 8

The following compounds were prepared according to the procedure of Example 5.

EXAMPLE 6

N-benzyl-3-(3,5-di-tert-butyl-4-hydroxybenzylidene)-2-pyrrolidone m.p.: 166° C.

NMR (δ, CDCl₃): 1.45 (18H, s), 2.9-3.1 (2H, m), 3.38 (2H, t, J=6 Hz), 4.62 (2H, s), 5.41 (1H, s) and 7.3-7.5 (8H, 7.31, 7.36).

EXAMPLE 7

N-propargyl-3-(3,5-di-tert-butyl-4-hydroxybenzylidene)-2-pyrrolidone m.p.: 212° C.

NMR (δ, CDCl₃): 1.46 (18H, s), 2.23 (1H, t, J=3 Hz), 2.9-3.2 (2H, m), 3.59 (2H, t, J=7 Hz), 4.26 (2H, d, J=3 Hz), 5.41 (1H, s) and 7.2-7.4 (3H, m).

EXAMPLE 8

N-(2-hydroxyethyl)-3-(3,5-di-tert-butyl-4-hydroxybenzylidene)-2-pyrrolidone 300 mg of N-2-(2-tetrahydropyranyloxy)ethyl-3-(3,5-di-tert-butyl-4-hydroxybenzylidene)-2-pyrrolidone was hydrolyzed with hydrochloric acid in methanol according to the procedure of Example 5 to give 150 mg of the title compound.

m.p.: 191° C.

NMR (δ, CDCl₃): 1.45 (18H, s), 2.9-3.2 (2H, m), 3.38 (1H, t), 3.5-3.7 (4H, m), 3.84 (2H, q, J=6 Hz), 5.41 (1H, s) and 7.2-7.4 (3H, m).

EXAMPLE 9

One embodiment of the novel intermediate compound, N-methoxy-3-bromo-2-pyrrolidone, was obtained by the below illustrated procedures and then used for the finish product.

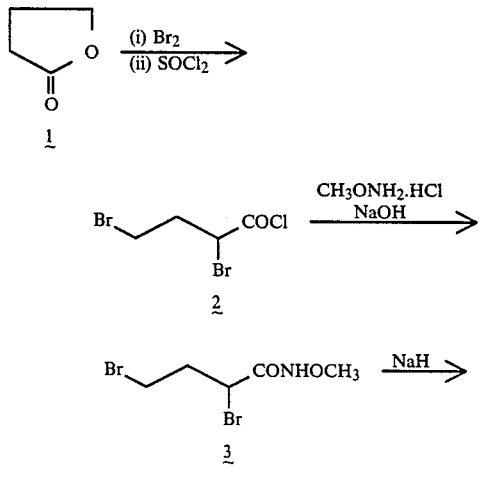

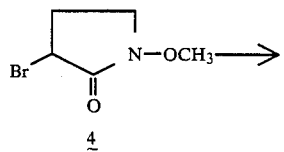

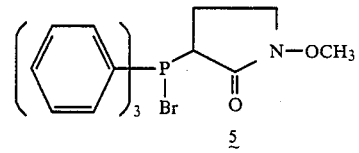

2,4-dibromobutanoyl chloride 2

A mixture liquid of 500 g of δ-butyrolactone and 10 ml of PBr3 was heated up to 100° C. Then 250 ml of bromine Br2 was slowly added dropwise into the mixture, not being exposed to the atmosphere, over a period of 6 hours, while the reaction mixture was agitated and kept at 110° to 115° C. After the addition, the reaction mixture was further stirred at the same temperature for 1 hour. Then it was cooled down to 90° C. 0.5 ml of dimethylformamide was added thereto. 500 ml of thionyl chloride was added thereto dropwise over 2 hours in an oil bath maintained at 90° C. The mixture was further stirred for 3 hours at the same temperature. The product liquid was distilled at 60° to 65° C. at 1 mmHg to obtain 1.0 kg of the title compound 2.

N-methoxy-2,4-dibromobutanamide 3

A mixture of 520 g of acetoamide, 1 liter of water and 5 liters of chloroform was cooled down to minus 5° C. with an ice-salt bath. A mixture of 1450 g of 2,4-dibromobutanoyl chloride and 1 liter of chloroform was added thereto. Then a solution of 500 g of sodium hydroxide in 1 liter of water was added thereto dropwise so that the reaction temperature was kept at a temperature of not higher than 10° C. After completion of the addition, the reaction mixture was further stirred for 1 hour at the same temperature. The chloroform phase was separated from the reaction mixture and washed with first 0.5N aqueous hydrochloric acid, second a saturated, aqueous sodium bicarbonate solution and third a saturated, aqueous salt solution. It was then dried with magnesium sulfate and the chloroform was distilled out to obtain 1400 g of oil as a residue. It was used, as it was, for the subsequent procedure.

N-methoxy-3-bromo-2-pyrrolidone 4

1400 g of a crude N-methoxy-2,4-dibromobutanamide was dissolved in 5 liters of benzene. Then 125 g of NaH was added little by little to the solution at 15° to 20° C. while the reaction mixture was cooled with an iced water bath. After the reaction, the remaining NaH was decomposed with ice and the product mixture was washed with a saturated, aqueous salt solution. It was dried with magnesium sulfate. Then benzene was distilled out. The product was purified with the column chromatography, using silica gel and a mixture of acetaone and benzene to obtain 500 g of the title compound 4.

NMR (δ, CDCl₃): 3-CH 4.38(1H, dd. J=3.6 Hz, 7.2 Hz) 4-CH2 2,2-2,9(2H, m) 5-CH2 3,4-3,9(2H, m) 1-CH3O 3,82(3H, s)

(N-methoxy-2-pyrrolidone-3-yl)triphenylphosphonium bromide 5

A mixture of 75 g of N-methoxy-3-bromo-2-pyrrolidone, 105 g of triphenylphosphine and 700 ml of tetrahydrofuran was heated and refluxed for 24 hours. After cooled, the resulting precipitates were taken with filtration and washed with tetrahydrofuran. Dried, 54 g of the title compound 5 was obtained.

The compound 5 was reacted in the same manner as shown in Example 3 to obtain the 2-pyrrolidone derivative of the invention.

The embodiments of the invention in which an exclusive property or privilege is claimed are defined as follows:

1. A 2-pyrrolidone derivative of the formula:

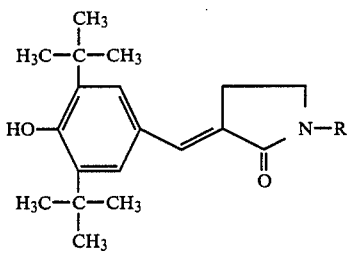

wherein R represents a hydrogen atom, a lower alkyl group having up to 6 carbon atoms, a lower alkoxy group having up to 6 carbon atoms, a lower alkynyl group having up to 6 carbon atoms or a group of the formula:

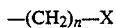

—(CH$_2$)$_n$—X wherein X represents a phenyl or a hydroxyl group or a group of the formula:

wherein R$^1$ and R$^2$ may be the same or different from each other and each represents a hydrogen atom or a lower alkyl group; and n represents an integer of 1 or 2: or a pharmaceutically acceptable salt thereof.

2. A 2-pyrrolidone derivative as set forth in claim 1, wherein R is a hydrogen atom.

3. A 2-pyrrolidone derivative as set forth in claim 1, wherein R is a lower alkyl group.

4. A 2-pyrrolidone derivative as set forth in claim 1, wherein R is a lower alkoxy group.

5. A 2-pyrrolidone derivative as set forth in claim 1, wherein R is a lower alkynyl group.

6. A 2-pyrrolidone derivative as set forth in claim 1, wherein R is a methoxy group.

7. A 2-pyrrolidone derivative as set forth in claim 1, wherein R is a methyl group.

8. A pharmaceutical composition which comprises a 2-pyrrolidone derivative as defined in claim 1 and a pharmaceutically acceptable carrier.

9. A pharmaceutical composition as claimed in claim 8, in which R is a lower alkoxy group.

10. A method for treating a patient suffering from an inflammatory disease, which comprises administering to said patient a therapeutically effective amount of a compound as defined in claim 1, in combination with a pharmacologically acceptable carrier, diluent or vehicle.

11. A method as claimed in claim 10, in which R is a lower alkoxy group.

12. A 2-pyrrolidone derivative as set forth in claim 1, wherein R is —(CH$_2$)$_n$—x.

13. A 2-pyrrolidone derivative as set forth in claim 12, wherein X is phenyl.

14. A 2-pyrrolidone derivative as set forth in claim 12, wherein X is hydroxyl.

15. A 2-pyrrolidone derivative as set forth in claim 12, wherein X is

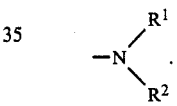

16. A 2-pyrrolidone derivative as set forth in claim 1 in which R is ethyl.

17. A 2-pyrrolidone derivative as set forth in claim 1 in which R is 2-dimethylaminoethyl.

18. A 2-pyrrolidone derivative as set forth in claim 1 in which R is benzyl.

19. A 2-pyrrolidone derivative as set forth in claim 1 in which R is propargyl.

20. A 2-pyrrolidone derivative as set foth in claim 1 in which R is 2-hydroxyethyl.

* * * * *